(12) United States Patent
Khanal

(10) Patent No.: US 7,878,967 B1
(45) Date of Patent: Feb. 1, 2011

(54) HEART FAILURE/HEMODYNAMIC DEVICE

(76) Inventor: Sanjaya Khanal, 37581 Emerald Forrest Dr., Farmington Hills, MI (US) 48331

( * ) Notice: Subject to any disclaimer, the term of this patent is extended or adjusted under 35 U.S.C. 154(b) by 716 days.

(21) Appl. No.: 11/244,845

(22) Filed: Oct. 6, 2005

(51) Int. Cl.
*A61M 1/10* (2006.01)
*F04D 3/00* (2006.01)

(52) U.S. Cl. .......................................... 600/16; 415/71

(58) Field of Classification Search ............. 600/16–18; 604/155; 623/3.14; 415/74, 72
See application file for complete search history.

(56) References Cited

U.S. PATENT DOCUMENTS

| | | | | |
|---|---|---|---|---|
| 4,919,647 A | * | 4/1990 | Nash | 600/16 |
| 4,995,857 A | * | 2/1991 | Arnold | 600/16 |
| 5,040,944 A | * | 8/1991 | Cook | 415/72 |
| 5,501,574 A | * | 3/1996 | Raible | 415/74 |
| 5,749,855 A | * | 5/1998 | Reitan | 604/151 |
| 6,083,260 A | * | 7/2000 | Aboul-Hosn | 623/3.14 |
| 6,533,716 B1 | * | 3/2003 | Schmitz-Rode et al. | 600/16 |
| 2003/0135086 A1 | * | 7/2003 | Khaw et al. | 600/16 |
| 2003/0187322 A1 | * | 10/2003 | Siess | 600/16 |

* cited by examiner

*Primary Examiner*—Carl H Layno
*Assistant Examiner*—Luther G Behringer
(74) *Attorney, Agent, or Firm*—Rader, Fishman & Grauer PLLC; James F. Kamp; Kristin L. Murphy

(57) ABSTRACT

An improved hemodynamic device may be collapsed and implanted percutaneously. The device includes at least one collapsible blade member and a rotary mover for rotating the blade member to provide hemodynamic circulation. In one embodiment of the invention, the blade member rotates within a basket after implantation. The basket may be formed of shape-memory wires.

19 Claims, 3 Drawing Sheets

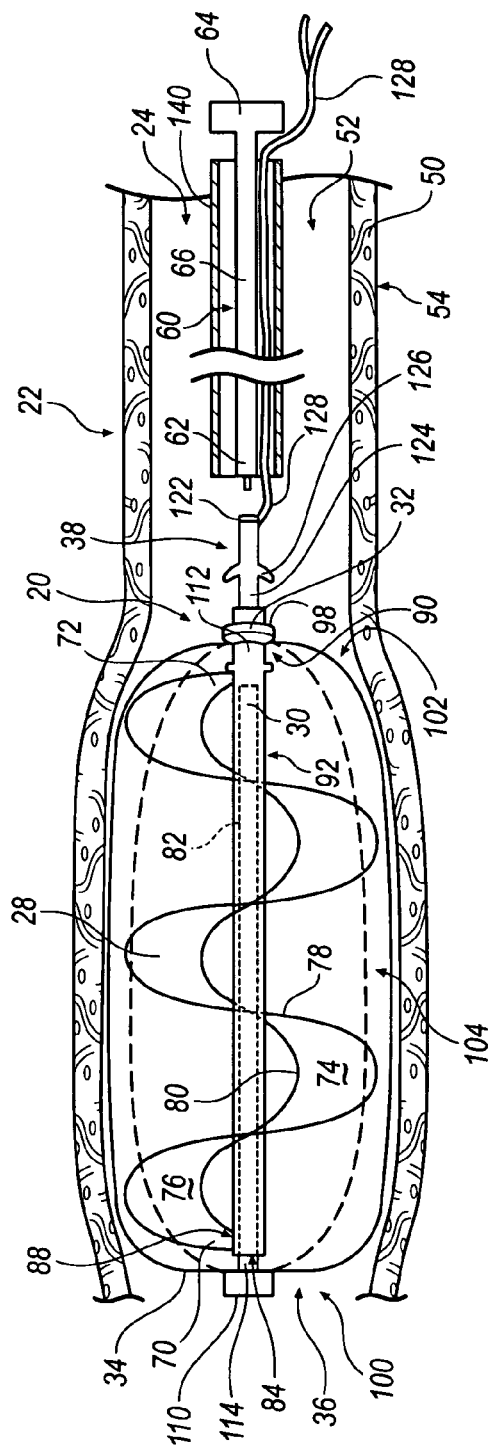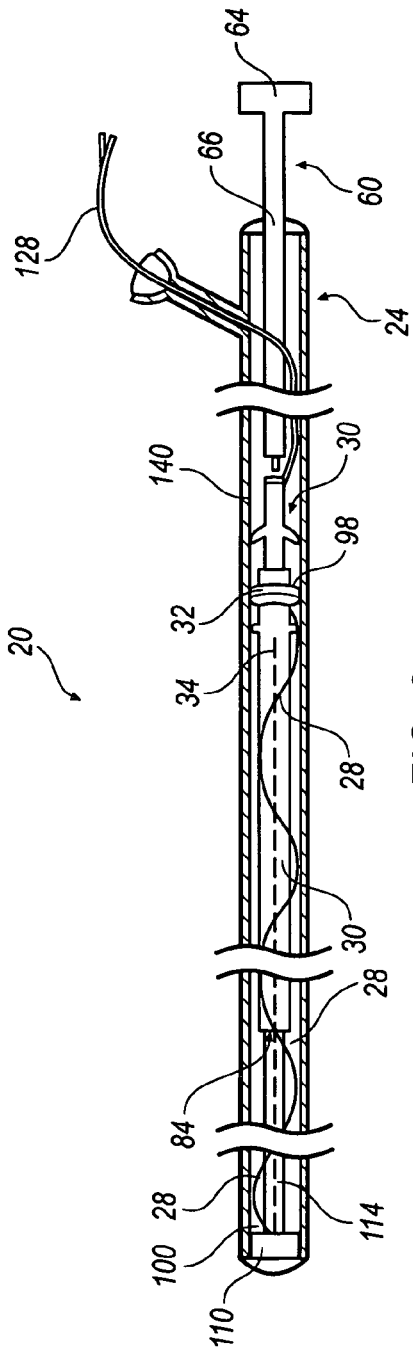

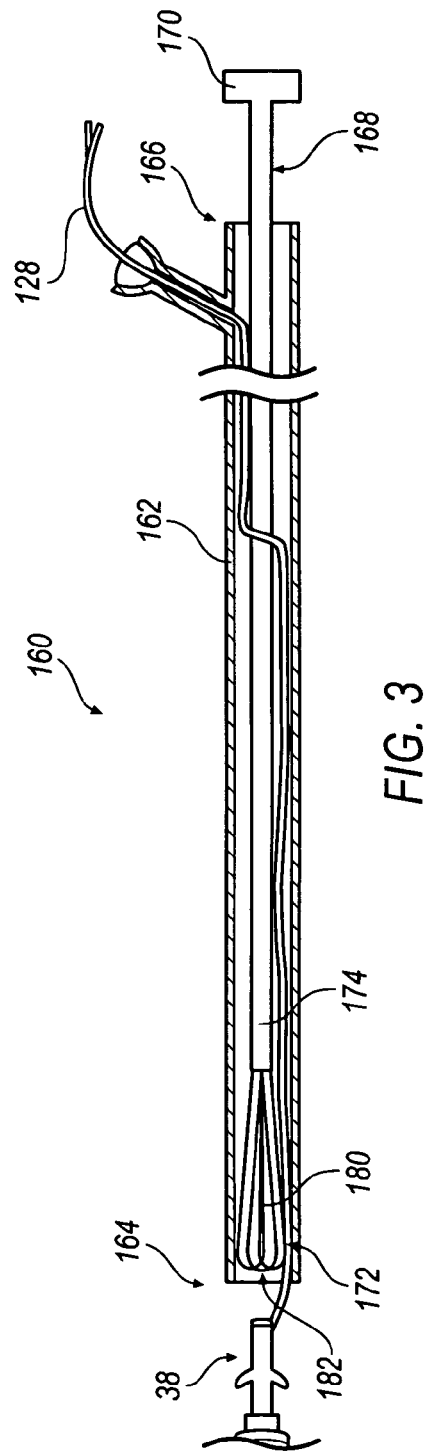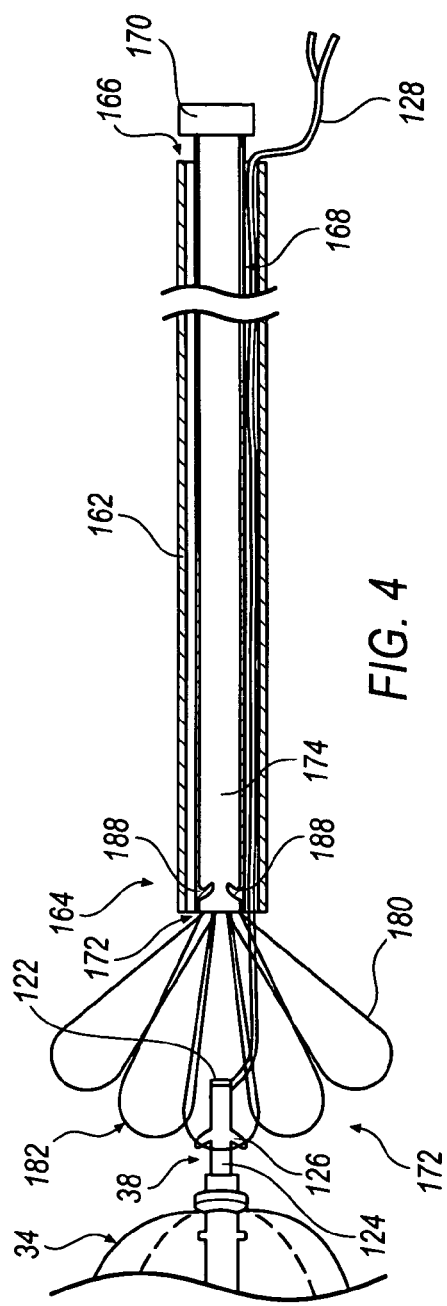

HEART FAILURE/HEMODYNAMIC DEVICE

TECHNICAL FIELD

The present invention relates generally to hematological pumps and more specifically to a collapsible hemodynamic assist device that may be implanted and/or removed in a minimally invasive procedure.

BACKGROUND

Chronic heart failure (CHF) is a leading cause of mortality and morbidity in the world. The prevalence of CHF s increasing as the population ages. While recent advances in the pharmacotherapy of congestive hearts have reduced this mortality and morbidity, a large number of patients develop progressive decompensated heart failure. Typically for CHF, a pump such as a ventricular assist device (VAD) is implanted in a patient awaiting a heart transplant. The VAD is implanted as a "bridge to transplant" for those weakened hearts that are expected to become unable to pump enough blood to sustain life. A VAD is typically attached to the left ventricle and draws blood from the left ventricle and sends the blood to the aorta. During the procedure to implant a VAD, the wall of the left ventricle must be opened, resulting in an interference with the operation of the left ventricle and little chance of cardiac recovery.

A cardiac recovery is possible for patients who suffer from CHF, especially through treatment with biopharmaceuticals (for example, growth factors, cytokines, myoblasts, and stem cells). The likelihood of cardiac recovery is believed to be increased by reducing the stress on the heart from the decompensated state. However, the existence of a VAD greatly reduces the likelihood of cardiac recovery from CHF. The scarcity of transplantable hearts further lessens the chances of recovery after a VAD has been implanted.

Therefore, there exists a need for a hemodynamic assist device that can be implanted without damaging the heart and preventing cardiac recovery.

SUMMARY OF THE INVENTION

An embodiment of the present invention provides a hemodynamic assist device including an elongated shaft generally defining an axis A-A and having a first end and a second end and a rotary mover coupled to the shaft adjacent the first end. The device also includes a collapsible blade member selectively rotatable by the rotary mover about the axis A-A and a lower support selectively coupled to at least one of the support members, wherein the lower support selectively supports a lower portion of the article.

Another embodiment of the present invention provides an implantable pump assembly including a rotary mover and a blade member coupled to at least a part of the rotary mover. The blade member is selectively transformable between a collapsed configuration and an expanded configuration. The pump assembly also includes an implantation device having a sheath. The sheath includes an inner surface for retaining the blade member generally in the collapsed configuration.

A further embodiment of the present invention provides an implantation device for a hydrodynamic device including a sheath for retaining a blade member in a collapsed configuration and a device uncoupling assembly selectively interposed within the sheath and selectively coupled to the hydrodynamic device.

An additional embodiment of the present invention provides an retrieval apparatus for a hydrodynamic device including a sheath and a retrieval assembly selectively coupled to the hemodynamic device and, at least partially, interposed within the sheath.

Another embodiment of the present invention provides a method of manufacturing an implantable hemodynamic assist device that includes providing a blade member and a rotary mover. The blade member is selectively transformable between a collapsed configuration and an expanded configuration. The method further includes collapsing the blade member into a desired configuration and interposing the blade member into a sheath. An internal dimension of the sheath is less than a corresponding external dimension of the blade member when the blade member is in the expanded configuration.

BRIEF DESCRIPTION OF THE DRAWINGS

The present invention will now be described, by way of example, with reference to the accompanying drawings, in which:

FIG. 1 illustrates a partial side view of a device according to an embodiment of the present invention.

FIG. 2 is a side view of the device of FIG. 1, illustrated in a collapsed configuration interposed within a delivery sheath.

FIG. 3 is a partial side view of a retrieval device for removing a device according to an embodiment of the present invention, illustrated in a collapsed configuration with a retrieval portion illustrated with a reduced diameter for clarity.

FIG. 4 is a partial side view of the retrieval device of FIG. 3, illustrated in an expanded configuration.

FIG. 5 is a partial side view of a device according to an embodiment of the present invention.

FIG. 6 is a side view of the device of FIG. 5, illustrated in a collapsed configuration.

DETAILED DESCRIPTION

Referring now to the drawings, the preferred illustrative embodiments of the present invention are shown in detail. Although the drawings represent some preferred embodiments of the present invention, the drawings are not necessarily to scale and certain features may be exaggerated or partially sectioned to better illustrate and explain the present invention. Further, the embodiments set forth herein are not intended to be exhaustive or otherwise limit or restrict the invention to the precise forms and configurations shown in the drawings and disclosed in the following detailed description.

Referring to FIG. 1 a hemodynamic assist device 20 is illustrated interposed within a blood transferring conduit such as a descending aorta 22 adjacent an implantation device 24. Device 20 includes a helical blade member 28, a shaft 30, a rotary mover 32, a plurality of wires 34 forming a basket 36, and a connection end 38. Aorta 22 includes a tubular wall 50 having an inside surface 52 and an outside surface 54. Implantation device 24, as discussed in greater detail below, includes a device uncoupling assembly 60 having a coupling end 62, a manipulating end 64, and a connecting portion 66 extending therebetween.

Blade member 28 includes a first blade end 70, a second blade end 72, a pumping surface 74, an opposing surface 76, an outer helical edge 78, and an inner helical edge 80. Shaft 30 includes a cylindrical inner surface 82 defining a guide aperture 84, a first shaft end 88, a second shaft end 90, and a generally cylindrical shaft surface 92 extending therebetween. The second blade end 72 is attached to the second shaft end 90.

Rotary mover 32 includes a rotor 96 (not shown) and a housing 98. In addition to wires 34, basket 36 includes a first basket end 100, a second basket end 102, and a longitudinal portion 104. The first basket end 100 includes a web portion 110. Second end 102 includes a coupling portion 112, which is coupled to outer housing 98. Web portion 110 includes a guide pin 114 that can axially telescope within the guide aperture 84 of the shaft 30.

In an expanded configuration (FIG. 1), the first basket end 100 and a second basket end 102 of each wire 34 is curved. In a collapsed configuration, the first basket end 100 and a second basket end 102 of each wire 34 are generally straight.

Connection end 38 includes a delivery portion 122 opposite a device connecting portion 124 with a retrieval portion 126 positioned therebetween. Connection end 38 also includes a wiring 128 extending therethrough. Coupling end 62 may be connected to implantation device 24, as discussed in greater detail below.

To briefly discuss the interconnections of device 20, basket 36 couples device 20 to the inside surface 52 of the tubular wall 50. The coupling portion 112 interconnect basket 36 to outer housing 98. Shaft 42, blade member 28, and rotor 96 are interconnected for rotation relative aorta 22. As blade member 28 rotates, blood is urged away from the heart (not shown) as at least a portion of the blood adjacent blade member 28 is directed by the pumping surface 74. Wiring 128 interconnects rotary mover 32 to a power source (not shown).

Preferably, wires 34 and blade member 28 are constructed of a shape memory material that will return to generally the expanded configuration shown in FIG. 1 after the device has been manipulated into the collapsed configuration of FIG. 2. Even more preferably, wires 34 and blade member 28 are constructed of Nitinol, which is a shape memory metal suitable for implantation.

In the embodiment illustrated, blood is urged generally parallel to the A-A axis from the first blade end 70 to the second blade end 72 and the first blade end 70 is closer to a left ventricle than the second blade end 72.

FIG. 2 further illustrates the implantation device 24 to include an implantation sheath 140, in addition to the device uncoupling assembly 60. Preferably, sheath 140 extends over the entire length of the device 20 while at least a portion thereof remains outside of the patient. In this manner, device 20 may be delivered to a desired delivery site while manipulation end 64 is operated by a user who requires only arthroscopic access.

In one embodiment of the operation of the implantation device 24, a patient is prepared for the implant. The implantation device 24, with a hemodynamic assist device 20 interposed therein, is inserted percutaneously through an artery, such as the femoral or brachial artery, until the device 20 is positioned within the descending aorta. The sheath 140 is retracted, or guided toward the manipulation end 64, exposing the device 20. The basket 36 expands as the first basket end 100 and a second basket end 102 of each wire 34 returns to the curved shape of the expanded configuration (FIG. 1). The sheath 140 is further retracted and wiring 128 may be connected to the power source.

As the wires 34 return generally to the curved shape of the expanded configuration of FIG. 1, the guide pin 114 axially translates within the guide aperture 84 of the shaft 30 to permit the web portion 110 to move closer to the coupling portion 112. While guide pin 114 is illustrated as a single pin that allows web portion 110 to axially translate with respect to shaft 30, guide pin 114 may be a multi-piece telescopic member that permits web portion 110 to axially translate away from connection end many times the length of shaft 30.

It would be appreciated that the wires 34 can only return to their unfettered shape if the internal diameter of the aorta 22 were sufficient to permit unimpeded shape rebound. Some restraint of the wires 34 from complete shape rebound is desired as wires 34 interfere with the inside surface 52 of aorta 22. This interference between longitudinal portions 104 of wires 34 causes wires 34 to couple with inside surface 52, thereby preventing rotation of basket 36 within aorta 22.

While blade member 28 is described as being attached to the first shaft end 88, blade member 28 may be attached to either end of shaft 30, or may be attached to both ends of shaft 30.

FIGS. 3 and 4 illustrate a retrieval apparatus 160. Retrieval apparatus 160 includes a retrieval sheath 162 having a distal end 164 and a proximal end 166, and a retrieval assembly 168 interposed therein. The retrieval assembly 168 includes a manipulation end 170, a coupling end 172, and a connecting portion 174 extending therebetween. Coupling end 172 includes a plurality of dispersed wire loops 180 having distal portions 182 and interconnected proximal ends 184. The distal portions 182 converge as wire loops 180 are drawn into the retrieval sheath 162. Coupling end 172 also includes a plurality of hooks 188 formed on an inside surface of the coupling end 172. Hooks 188 engage retrieval portion 126 for removal of device 20, as discussed below.

As best seen in FIG. 4, the wire loops 180 will at least partially encompass second basket end 102 of device 20 as the wire loops 180 converge. In this manner, debris, such as clots, may be captured and pulled into sheath 162 as device 20 is removed. In the embodiment illustrated, wire loops 180 form a diameter slightly larger than the second basket end 102, although wire loops may be longer or shorter, or tailored for specific applications, as desired.

In one embodiment of the operation of the retrieval apparatus 160, wiring 128 of an implanted device 20 that is desirably removed is located and inserted through the distal end 164 of retrieval sheath 162. The retrieval apparatus 160 is then guided to device 20 as wiring 128 threads through sheath 162. When distal end 164 has reached the device 20, sheath 162 is retracted slightly, such as between 5 and 15 mm, to permit wire loops 180 to extend past distal end 164 and diverge to a diameter preferably greater than the second basket end 102.

To retract the sheath 162, a user may restrict movement of manipulation end 170 while guiding sheath 160 toward manipulation end 170. The retrieval apparatus 160 is then guided toward device 20 until the coupling end 172 of retrieval device 160 contacts the retrieval portion 126 of device 20. As coupling end 172 is further guided toward device 20, delivery portion 122 is guided into the coupling end 172. Moving coupling end 172 further toward device 20 results in hooks 188 traveling beyond retrieval portion 126. Hooks 188 engage retrieval portion 126 to provide a connection between retrieval assembly 168 and device 20 suitable for drawing device 20 into sheath 162. A click may be heard or a sensation may be felt through manipulation end 170 as hooks 188 engage retrieval portion 168.

Manipulation end 170 is then guided away from sheath 162, causing the wire loops 180 to partially enter sheath 162 and converge onto the second basket end 102 of device 20. Manipulation end 170 may be further guided away from sheath 162 until the device 20 is collapsed into sheath 162. As device 20 is collapsed into sheath 162, blade member 28 and other collapsible portions of device 20 are transformed into the collapsed configuration.

While the profile of hooks 188 are illustrated in FIG. 4, in the embodiment illustrated, coupling end 172 has two hooks 188 that preferably extend at least 90° around the inside circumference of coupling end 172, although coupling end 172 may include any number of hooks 188 of preselected arcuate width to adequately couple with retrieval portion 126. Also, retrieval portion 126 may be annular, extending around the circumference of connection end 38, or may be segmented into a series of extensions with the general profile illustrated in FIG. 4.

Figures 5, 6:
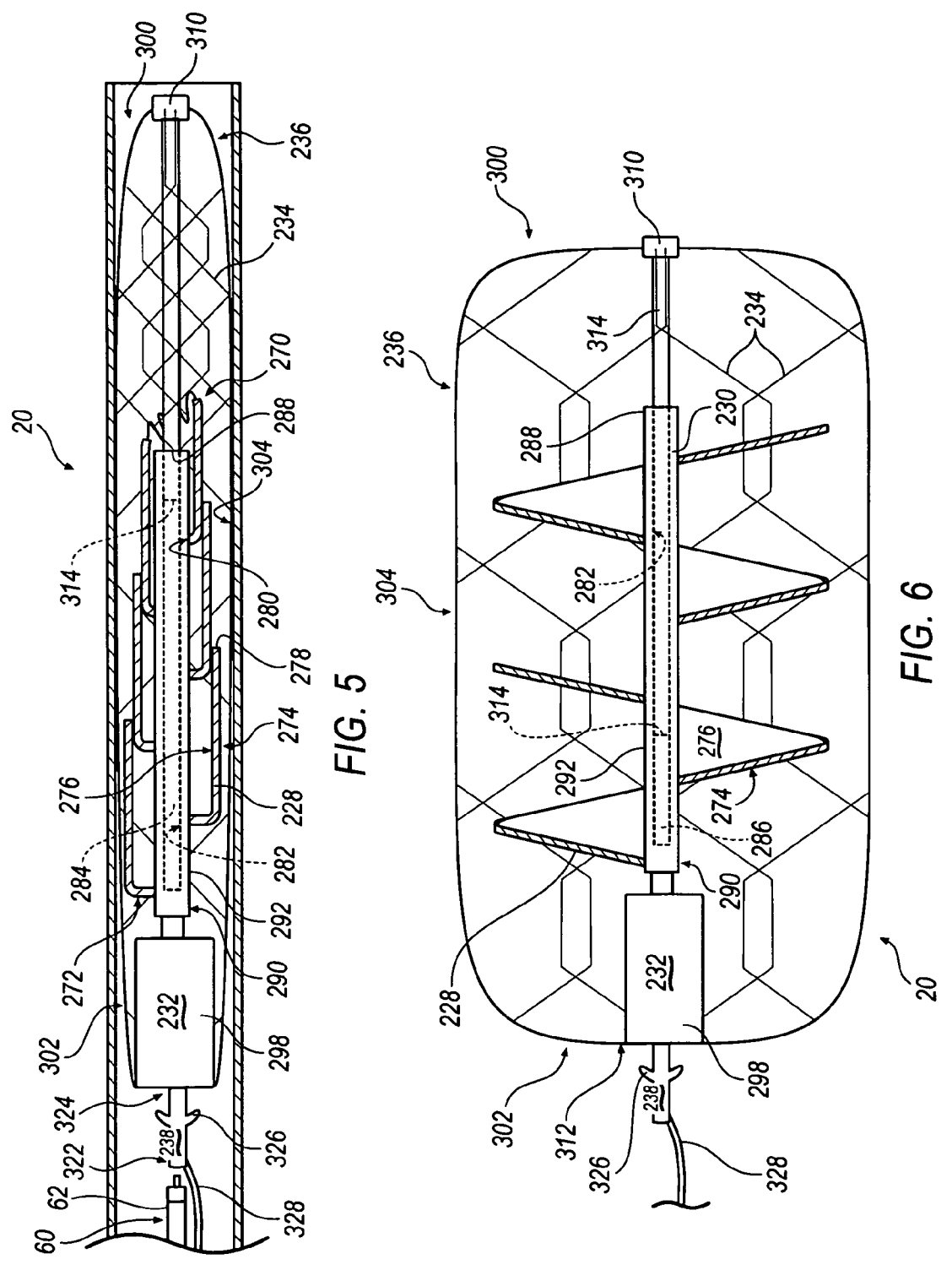

FIGS. 5 and 6 illustrate an alternative embodiment of the device 20 as a hemodynamic assist device 220. FIG. 5 illustrates device 220 in a collapsed configuration interposed within an implantation device 224. FIG. 6 illustrates device 220 in an expanded configuration. Device 220 includes a helical blade member 228, a shaft 230, a rotary mover 232, a plurality of wires 234 forming a basket 236, and a connection end 238. Implantation device 224 is substantially similar to implantation device 24, as discussed above.

Blade member 228 includes a first blade end 270, a second blade end 272, a pumping surface 274, an opposing surface 276, an outer helical edge 278, and an inner helical edge 280. Shaft 230 includes a cylindrical inner surface 282 defining a guide aperture 284, a first shaft end 288, a second shaft end 290, and a generally cylindrical shaft surface 292 extending therebetween. The first blade end 270 is attached to the first shaft end 288.

Rotary mover 232 includes a rotor 296 (not shown) and a housing 298. In addition to wires 234, basket 236 includes a first basket end 300, a second basket end 302, and a longitudinal portion 304. The first basket end 300 includes a web portion 310. Second end 302 includes a coupling portion 312, which is coupled to outer housing 298. Web portion 310 includes a guide pin 314 that can axially telescope within the guide aperture 284 of the shaft 230.

In an expanded configuration (FIG. 6), the first basket end 300 and a second basket end 302 of each wire 234 is curved. In a collapsed configuration, the first basket end 300 and a second basket end 302 of each wire 234 are generally straight with slight curvature.

Connection end 238 includes a delivery portion 322 opposite a device connecting portion 324 with a retrieval portion 326 positioned therebetween. Connection end 38 also includes a wiring 328 extending therethrough. Delivery portion 322 may be connected to implantation device 224, as discussed in greater below.

To briefly discuss the interconnections of device 220, basket 236 couples device 220 to the inside surface 52 of the tubular wall 50 (as best seen in FIG. 2). The coupling portion 312 interconnect basket 236 to outer housing 298. Shaft 242, blade member 228, and rotor 296 are interconnected for rotation relative aorta 22. As blade member 228 rotates, blood is urged away from the heart (not shown) as at least a portion of the blood adjacent blade member 228 is directed by the pumping surface 274. Wiring 328 interconnects rotary mover 232 to a power source (not shown).

Similar to the materials above, wires 234 and blade member 228 are constructed of a shape memory material that will return to generally the expanded configuration shown in FIG. 6 after the device has been manipulated into the collapsed configuration of FIG. 5. Even more preferably, wires 234 and blade member 228 are constructed of Nitinol.

Implantation and retrieval of device 220 is accomplished in similar fashion as implantation and retrieval of device 20 described herein. Preferably, retrieval apparatus 160 can be used to retrieve device 220.

While the coupling end 172 is coupled to the hemodynamic device by operation of said manipulation end 170, the connecting portion 174 may be any item that transmits a guiding force between the manipulation end 174 and the coupling end 172. For example, connecting portion 174 may be a flexible shaft or a working fluid capable of causing a desired operation at the coupling end 172 by manipulation of the fluid pressure.

Blade members 28, 228 may be a foldable, stretchable, and/or coilable blade or a plurality of elongated components that perform in conjunction to assist the flow of blood along axis A-A.

In addition to a power source, the rotary mover may by interconnected to a control system for control of the device 20, 220. The control system may be operable to increase the angular velocity of blade member 28 in response to various parameters such as, for example, heart rate, and blood pressure. Additionally, a stress test of the patient or other test that provides relevant information may be used to determine desired operational parameters of the device 20.

Once a sheath, such as the implantation sheath 140 is positioned for delivery of a hemodynamic assist device 20, a basket, such as basket 36, may be implanted, and then the uncoupling assembly 60 may be removed from the sheath to allow further portions of a hemodynamic assist device to be inserted through the length of the sheath to effect a delivery in two distinct steps.

While blade members 28, 228 are described as a continuous piece of material, blade members 28, 228 may be a plurality of wires that will return to a desired configuration to form a plurality of helical surfaces that may be rotated to effect a desired pumping action While devices 20, 220 are preferably implanted into the aorta in order to provide the maximum benefit while not damaging the heart so as to prevent cardiac recovery, devices 20, 220 may be implanted into other fluid conduits, including those that do not normally transfer blood.

While the invention has been described with respect to specific examples including preferred modes of carrying out the invention, those skilled in the art will appreciate that there are numerous variations and permutations of the above described systems and techniques that fall within the spirit and scope of the invention as set forth in the appended claims.

What is claimed is:

1. A hemodynamic assist device comprising:
an elongated shaft portion generally defining an axis A-A and having a first shaft end and a second shaft end and a guide aperture having a closed proximal end, the guide aperture extending at least partially between the first shaft end and the second shaft end;
a rotary mover coupled to said shaft portion adjacent said first shaft end;
a collapsible blade member disposed substantially along the length of said shaft portion, wherein said blade member is defined by a first blade end member and a second blade end member, wherein said first blade end member is connected to said shaft portion adjacent said first shaft end and wherein said second blade end member is connected to said shaft portion and wherein said blade member includes an inner helical edge and at least a portion of said inner helical edge is not coupled to said shaft portion along its length between said first blade end member and said second blade end member so as to define a gap between said inner helical edge and an outer surface of said shaft portion, wherein said blade member is selectively rotatable by said rotary mover about the axis A-A; and
a guide member having a guide member proximal end and a guide member distal end, wherein the guide member proximal end is interposed within the guide aperture in a telescoping manner such that the guide member is axially moveable within the guide aperture such that the guide member is moveable relative to the shaft portion.

2. The device of claim 1, wherein said blade member is constructed of a shape-memory material.

3. The device of claim 1, wherein said blade member is constructed, at least in part, of Nitinol.

4. The device of claim 1, wherein said shaft is coupled to at least a portion of said rotary member for rotation therewith.

5. The device of claim 1, wherein said blade member is coupled to said second shaft end for rotation therewith.

6. The device of claim 1, wherein said blade member is defined at least in part, by a thickness of less than 1 mm.

7. The device of claim 1, wherein said blade member selectively has a helical pumping surface and said helical pumping surface imparts a motive force on a fluid as said blade member rotates.

8. The device of claim 1, wherein said inner helical edge is intermittently connected to said shaft at least at portions along the length of said inner helical edge.

9. The device of claim 1, wherein said blade member is selectively elongated when in a collapsed configuration.

10. The device of claim 1, wherein said blade member is selectively folded, at least in part, when in a collapsed configuration.

11. The device of claim 1, further comprising a plurality of strut members, wherein said blade member is selectively interposed within at least a portion of said strut members.

12. The device of claim 11, wherein said strut members are positioned to form a basket, said device is selectively implanted within a blood transferring conduit, and said basket reduces the interference between the blade member and the blood transferring conduit.

13. The device of claim 11, wherein said strut members are constructed, at least in part, of Nitinol.

14. The device of claim 11, wherein said strut members are formed of wires.

15. The device of claim 12, wherein a first end of the basket is selectively coupled to a portion of said rotary mover and a second end of the basket is selectively coupled to the guide member distal end such that the second end of the basket will move toward the first end of the basket as the guide member telescopes within the guide aperture of said shaft portion.

16. The device of claim 1, wherein said rotary mover is an electric motor.

17. The device of claim 1, wherein said rotary mover is defined, at least in part, by an outer diameter of less than about 6 mm.

18. The device of claim 1, wherein said rotary mover is defined, at least in part, by an outer diameter of about 2 mm.

19. The device of claim 1, wherein said rotary mover includes an inner shaft and an outer housing.

* * * * *